(12) United States Patent
Blasi et al.

(10) Patent No.: US 6,333,784 B1
(45) Date of Patent: Dec. 25, 2001

(54) ESCA/RAMAN SPECTROSCOPY SYSTEM FOR THE ANALYSIS OF METAL CORROSION PRODUCTS

(75) Inventors: Raymond J. Blasi, Harrison City; David A. Allison, Bethel Park, both of PA (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 0 days.

(21) Appl. No.: 09/459,536

(22) Filed: Dec. 13, 1999

(51) Int. Cl.[7] ................. G01J 3/44; G01N 21/65
(52) U.S. Cl. ............................. 356/72; 356/301
(58) Field of Search ................. 356/72, 73, 301

(56) References Cited

U.S. PATENT DOCUMENTS 5,422,304 * 6/1995 Kohiki et al. .................. 438/95

FOREIGN PATENT DOCUMENTS 1-138109-A * 5/1989 (JP).
6-45288-A * 2/1994 (JP).

OTHER PUBLICATIONS

J. Gui et al, "In SITU Vibrational Spectra of the Passive Film on Iron in Buffered Borate Solution", Corrosion Science, vol. 32 No. 10 99–1105–1124, 1991.

* cited by examiner

Primary Examiner—F. L. Evans
(74) Attorney, Agent, or Firm—Virginia B. Caress; Paul A. Gottlieb

(57) ABSTRACT

An analytical instrument for performing ESCA and Raman measurements, having a vacuum chamber and a sample holder. The ESCA/Raman system enables the rapid acquisition of the molecular information from both homogeneous and heterogeneous corrosion films and deposits on metal specimens.

8 Claims, 3 Drawing Sheets

ESCA/RAMAN SPECTROSCOPY SYSTEM FOR THE ANALYSIS OF METAL CORROSION PRODUCTS

BACKGROUND OF THE INVENTION

1. Field of the Invention

The Government has rights in this invention pursuant to a contract awarded by the Department of Energy.

This invention relates to the field of analytical testing of the chemical composition of a sample. In particular, the present invention relates to a device for performing Electron Spectroscopy for Chemical Analysis (ESCA) and Raman spectroscopic studies.

2. Background of the Invention

The molecular composition of corrosion films and deposits on metal surfaces has been of interest for many years. In particular, it is well known that the life of a power generation plant can be extended if corrosion can be controlled to a point of minimization or elimination. To control corrosion, the corrosion products must first be accurately identified. This information can then be used with supplemental process information to identify and arrest the chemical mechanism from which corrosion products form in a system. Typically, corrosion products on metal surfaces are characterized by a combination of a host of analytical techniques which include, in part, Auger, X-ray Diffraction (XRD), Electron Spectroscopy for Chemical Analysis (ESCA), and most recently, Raman spectroscopy. Each of these analytical techniques provides a limited amount of information and neither technique alone can be used to unambiguously identify the compounds present in a corrosion film or deposit. For example, Auger provides elemental information that requires the analyst to hypothesize a molecular composition which must be confirmed by a secondary technique. XRD provides molecular composition information but is highly sensitive to (1) material concentration (the limit of detection is approximately 2–3%), (2) material composition (the technique cannot detect. amorphous material), and (3) sample geometry (sample face curvature and roughness degrade the spectra). As a result, the XRD technique cannot be used to unambiguously determine the true molecular composition of a corrosion product. The ESCA technique provides direct molecular composition information on all types of materials (including amorphous materials) by measuring molecular field dependent binding energies of atoms, but can not readily distinguish between various oxidization states of some elements such as iron (ESCA cannot accurately distinguish between $Fe^{2+}$ and $Fe^{3+}$). Because most corrosion products in a power generation plant consist of iron oxides and various doped iron oxides, the ESCA technique can only be used to speculate on the true molecular nature of iron oxide compounds present in a corrosion product from such a system. Finally, Raman spectroscopy provides molecular information on all types of materials (including amorphous materials and glasses) but cannot detect molecules that are not amenable to an internal dipole change (such as $Cu_2S$). As a result, it cannot be guaranteed that the Raman technique will detect all compounds present in a corrosion product.

ESCA and Raman spectroscopy synergistically complement each other in the chemical analysis of corrosion products on metal surfaces. In this case, molecular composition analysis information that cannot be obtained by one technique can be obtained by the other to give the most complete and unambiguous analysis of a corrosion product sample. For example, ESCA cannot readily distinguish between $Fe^{2+}$ and $Fe^{3+}$ based compounds whereas Raman spectroscopy produces well resolved unique vibrational fingerprint. spectra for most $Fe^{2+}$ and $Fe^{3+}$ corrosion product compounds such as $\alpha$-FeOOH, $\beta$-FeOOH, $\gamma$-FeOOH, $Fe(OH)^2$, $Fe_2O_3$ and $Fe_3O_4$. As a second example, ESCA can identify that a material contains phosphorus and oxygen but cannot distinguish between the various types of phosphates such as $PO_4^{3-}$, $HPO_4^{2-}$, and phosphate from $NaFePO_4$. Raman, on the other hand, produces clearly defined spectra for these species. Finally, and in contrast, ESCA can identify compounds such as $Cu_2S$ which cannot be detected by the Raman technique because such symmetrical compounds are not amenable to internal dipole changes which are needed for Raman analyses. Therefore, these two techniques synergistically complement each other and the integration of these two techniques results in a powerful analytical tool what will enable rapid, accurate, and unambiguous identifications of the chemical compositions of corrosion films or deposits in one single analysis without the need to use any other analytical techniques to confirm the results.

It is impractical to perform ESCA and Raman measurements on separate ESCA and Raman instruments because (1) the need to break the high vacuum of the ESCA instrument to transfer the sample to the Raman spectrometer will subject any newly exposed corrosion product to oxidizing room air which will compromise the sample integrity and produce erroneous results, and (2) the inability to accurately position the sample on both instruments so that both techniques are obtaining data from precisely the same location on the specimen.

Accordingly, a need remains for an integrated analytical instrument in which both ESCA and Raman measurements can be performed without exposing samples to air, and without the need for repositioning the sample between ESCA and Raman measurements. An integrated ESCA/Raman analytical instrument is one in which both ESCA and Raman analyses are performed on corrosion products on specimens located in a vacuum chamber. The ESCA/Raman system enables the rapid acquisition of molecular corrosion films and deposits on metal specimens.

SUMMARY OF THE INVENTION

In order to meet this need, the present invention is an integrated ESCA/Raman analytical instrument in which both ESCA and Raman analyses are performed on corrosion products on specimens located in a vacuum chamber. The instrument contains the hardware required to perform both techniques, including an X-ray source, an electron lens, an electron detector, an ion gun, a fiber optic probe linked to a laser light source, and a fiber optic probe linked to a monochromator and a visible light detector. The ion gun is used to sputter through films and deposits on metal surfaces. The sputtering can be done incrementally, so that both ESCA and Raman results can be obtained at various levels within the sample to obtain a cross-sectional composition profile. In ESCA analysis of a given level, the X-ray source produces X-rays of various energies which, when aimed at a sample, cause the sample to eject electrons. These ejected electrons are collected and counted by the electron lens and detector, respectively. The energies of the ejected electrons are used to identify the elements present, and the numbers of the ejected electrons are used to quantify the elements present. Monochromatic light from the laser, transmitted through a laser fiber optic cable, is directed through a laser light delivery probe and focused by lenses onto the sample. The resulting Raman scattered light emitted by the sample is collected by lenses and transmitted into a scattered light collection probe and a monochromator fiber optic cable to a monochromator and a detector. The absolute energies of the Raman shift peaks are used to identify the molecular composition of the material causing the Raman spectrum, and the intensities of the peaks can be used to quantify the material.

The ESCA/Raman analytical instrument can be used to obtain rapid chemical molecular information from films and deposits on any material surface. In particular, an ESCA/Raman system is of value for, among other applications, evaluating corrosion deposits and films formed on metal component surfaces from power generation plants. Typically, ESCA is used to sputter through films and deposits on metal surfaces and to perform molecular compound profiling of the corrosion material which may be layered. Sputtering is performed in step increments through the films or deposits. ESCA is performed at each step increment to obtain molecular composition depth profiling. This process is repeated until base metal is reached. Raman spectroscopy is performed along with ESCA at each incremental sputter depth. The ESCA/Raman data combined allow for a more accurate, conclusive, and uncompromised molecular composition profile as compared to information obtained from each analytical technique separately.

DETAILED DESCRIPTION OF THE PREFERRED EMBODIMENTS

Figure 1:
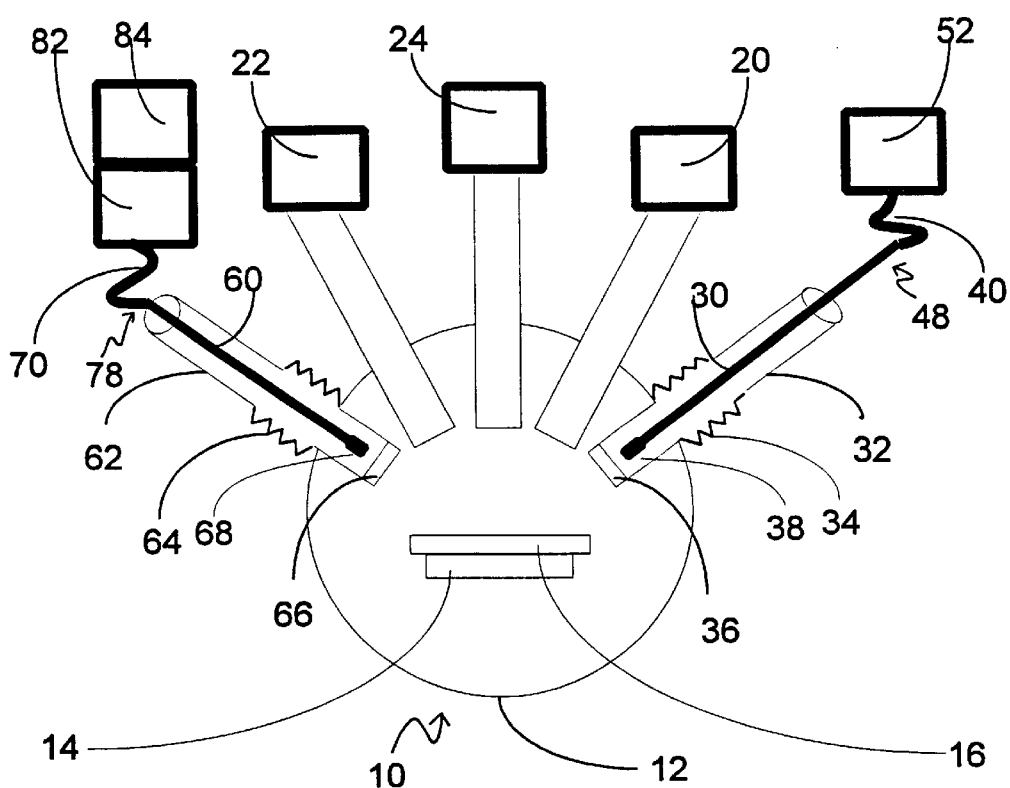
FIG. 1 is an exploded schematic diagram of the ESCA/Raman analytical instrument of the present invention.

The ESCA/Raman analytical instrument of this invention is the integration of ESCA hardware and Raman spectroscopy hardware into one single analysis unit. A schematic diagram of the disclosed system is shown in FIG. 1. An ESCA/Raman analytical instrument 10 made in accordance with the present invention includes a vacuum chamber 12, which houses a sample holder 14, which supports a sample 16. The sample holder 14 has micro positioning capabilities currently known to this art.

Other components, housed on vacuum chamber 12, of ESCA/Raman analytical instrument 10 used to obtain ESCA data, are an ESCA ion gun 20, an ESCA X-ray source 22 and an ESCA electron lens and detector 24.

To obtain ESCA data, sample 16 is placed on sample holder 14 in vacuum chamber 12, and a vacuum of approximately $1 \times 10^{-9}$ torr is achieved through a vacuum pump (not shown). The ESCA ion gun 20 is then used to bombard the sample surface with high energy ions 500–10,000 volts, preferable 4,000–5,000 v.s for our samples) to create freshly exposed corrosion material on the specimen surface. This process is called the sputtering process and can be used to selectively remove ultra thin layers of corrosion products from the surface of the corrosion specimen whose thickness can be as small as a few micrometers. Removing these ultra thin layers in a vacuum assures that the newly exposed corrosion products will not react with oxygen that is in laboratory air to create new compounds that were not created by the corrosion process. The freshly exposed material is then bombarded with any energy X-rays from ESCA X-ray source 22 (i.e. Mg $K_2$, Alk$_2$, etc.) to eject electrons from the electron clouds of the surface molecules of the corrosion material. These electrons are then collected in the electron lens and detector 24, where their numbers and energies are determined by techniques known in the art, for example with the use of a concentric hemispherical analyzer (CHA). The energies of the ejected electrons are used to identify the atoms or molecules from which they were ejected and the total integrated count is used to quantify the material identified as being present.

Monochromatic light for Raman analysis is supplied by a laser light delivery probe 30, which is housed in a delivery probe vacuum well 32, fitted with delivery probe bellows 34. The delivery probe bellows 34, which connects the delivery probe vacuum well 32 to the wall of the vacuum chamber 12, allows for axial positioning of the end of the well with respect to the sample surface. The delivery probe vacuum well 32 is terminated by a delivery probe optical window 36. In use, the laser light delivery probe 30 is inserted into the delivery probe vacuum well 32 until a laser light delivery probe distal end 38 touches the delivery probe optical window 36. The laser light delivery probe distal end 38 is shown in more detail in FIG. 2. A single strand fiber 40 in laser light delivery probe 30 directs monochromatic light through a bandpass filter 42 and delivery probe focusing lenses 44. A laser light delivery probe fiber sheath 46 defines an outer housing of the laser light delivery probe 30, as shown in FIG. 1. A laser light delivery probe proximal end 48 is optically linked to a laser light source 52.

Figure 3:
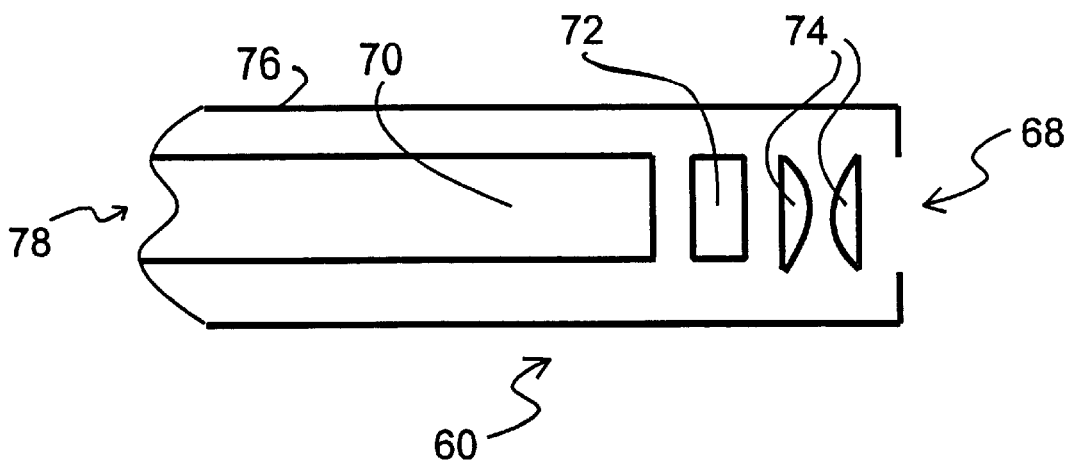
FIG. 3 is a schematic representation of the components of the Raman collection probe.

The scattered light representing the spectrum of sample 16 is collected in a scattered light collection probe 60, which is housed in a collection probe vacuum well 62, fitted with collection probe bellows 64. The collection probe bellows 64, which connects the collection probe vacuum well 62 to the wall of the vacuum chamber 12, allows for axial positioning of the end of the well with respect to the sample surface. The collection probe vacuum well 62 is terminated by a collection probe optical window 66. In use, the scattered light collection probe 60 is inserted into the collection probe vacuum well 62 until a scattered light collection probe distal end 68 touches the collection probe optical window 66. The scattered light collection probe distal end 68 is shown in more detail in FIG. 3. A multiple strand fiber optic bundle 70, contained within scattered light collection probe 60, is terminated at scattered light collection probe distal end 68 by a notch filter 72 and collection probe focusing lenses 74. A collection probe fiber sheath 76 defines an outer housing of the scattered light collection probe 60. A scattered light collection probe proximal end 78 is optically linked to a monochromator 82 and a detector 84.

Figure 2:
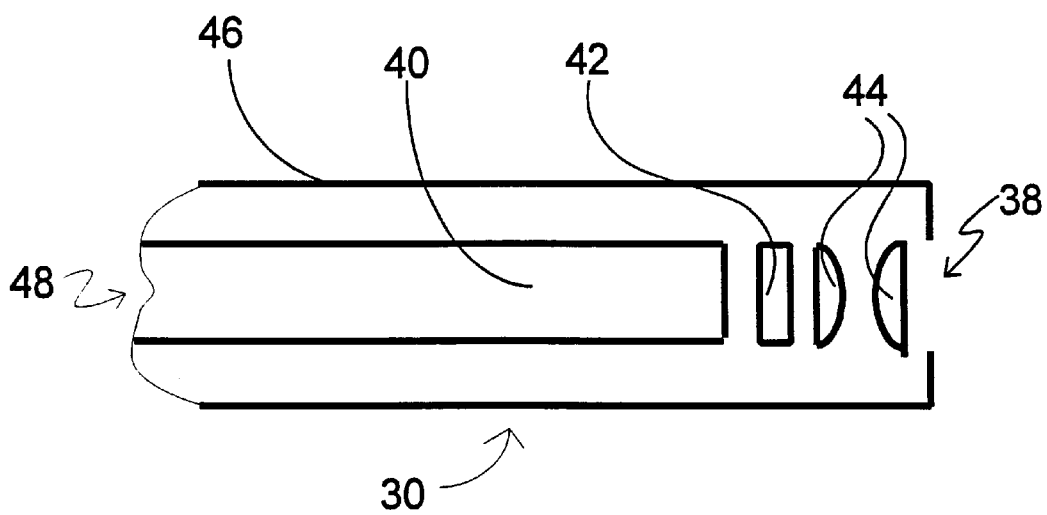
FIG. 2 is an exploded schematic representation of the components of the laser delivery probe.

To obtain Raman data, monochromatic light from the laser light source 52 is launched or emitted into single strand fiber 40 contained in laser light delivery probe 30. In the single strand fiber 40, some of the light interacts with the fiber optic material (typically $SiO_2$) to create a Raman spectrum of the fiber optic material. This Raman spectrum then co-propagates with the laser light and exits the fiber optic with the laser light. If the Raman spectrum of the fiber material is not filtered at this point, it will propagate into the analysis area where it will be reflected into the collection fiber probe resulting in a high background spectrum. However, bandpass filter 42 allows only monochromatic light to pass and rejects the Raman spectrum of the fiber optic, as shown in FIG. 2. Hence, monochromatic laser light without the superimposed fiber optic spectrum exits the probe. The laser light exiting the probe is focused and collimated by the delivery probe focusing lenses 44. The monochromatic laser light then passes through the delivery probe optical window 36 on the end of the delivery probe vacuum well 32 to impinge on the surface of the sample 16. The delivery probe vacuum well 32 is positioned so the laser light impinges the sample surface coincident with the spot analyzed by ESCA.

When the monochromatic light strikes the sample surface, the Raman spectrum of the surface layer of the corrosion material is generated. Also, unused laser light is Rayleigh scattered without creating a Raman spectrum. Both the Rayleigh scattered light and the Raman scattered light propagate to the collection probe vacuum well 62 where they pass through the collection probe optical window 66. The collection probe focusing lenses 74 define the field of view of the scattered light collection probe 60 and ensure that the collected light enters a notch filter 72 and the multiple strand fiber optic bundle 70 within the appropriate angles defined by the notch filter impingence angle specifications and the coherent fiber bundle numerical aperture. The notch filter 72 prevents the formation of the Raman spectrum of the fiber optic material in the collection probe by rejecting the Rayleigh scattered monochromatic laser light and allowing the Raman spectrum of the sample to pass into the scattered light collection probe 60. The multiple strand fiber optic bundle 70 contained within scattered light collection probe 60 has coherent imaging capabilities, so that Raman spectrum and video image information are transmitted to monochromator 82 for spectral processing. Alternatively, the scattered light can be used to obtain video images of the specimen surface when connected to a TV camera. If the monochromator 82 is used, it disperses the Raman scattered light, which is then detected by the detector 84. The absolute energies of the Raman shift peaks are used to identify the molecular composition of the material causing the Raman spectrum, and the intensity of the peaks can be used to quantify the material, as is known in the art.

The ability of Raman spectroscopy and ESCA to characterize corrosion films and surface areas near cracks of metal components and in wastage areas of metal components has already been demonstrated individually through several routine analyses of these types of samples. When combined, the two techniques are complementary; each technique alleviates drawbacks associated with the other.

The integrated ESCA/Raman system enables the rapid acquisition of molecular information from both homogeneous and heterogeneous corrosion films and deposits on metal specimens. In the integrated system, it is no longer necessary to expose the sample to air or to reposition it between measurements.

Having described the currently preferred embodiment of the present invention, it is to be understood that the invention may be otherwise embodied the scope of the appended claims.

We claim:

1. A device for performing Raman measurements, comprising:
   a vacuum chamber;
   a sample holder, mounted within the vacuum chamber;
   an ion gun, mounted within the vacuum chamber;
   a laser light delivery probe, mounted within the vacuum chamber;
   a scattered light collection probe, mounted within the vacuum chamber;
   a laser, optically linked to the laser light delivery probe;
   a monochromator, optically linked to the scattered light collection probe; and
   a light detector, optically linked to the monochromator.

2. A device for performing ESCA and Raman measurements, comprising:
   a vacuum chamber;
   a sample holder, mounted within the vacuum chamber;
   an ESCA measuring device in communication with the vacuum chamber; and
   a Raman measuring device in communication with the vacuum chamber.

3. A device for performing ESCA and Raman measurements, comprising:
   a vacuum chamber;
   a sample holder; mounted within the vacuum chamber;
   an X-ray source, in communication with the vacuum chamber;
   an electron detector, in communication with the vacuum chamber;
   an ion gun, in communication with the vacuum chamber;
   a laser light delivery probe, in communication with the vacuum chamber; and
   a scattered light collection probe, in communication with the vacuum chamber.

4. The device according to claim 3, in which the sample holder has micro positioning capabilities.

5. The device according to claim 3, further comprising a laser light source optically connected to the laser light delivery probe and a monochromator optically connected to the scattered light collection probe.

6. The device according to claim 5, further comprising:
   laser delivery focusing lenses, located at the end of the laser light delivery probe distal to the laser;
   a laser delivery optic window, located at the end of the laser light delivery probe distal to the laser;
   a bandpass filter, located at the end of the laser light delivery probe distal to the laser;
   a collection optic window, located at the end of the scattered light collection probe distal to the monochromator;
   a collection focusing lens, located at the end of the scattered light collection probe distal to the monochromator; and
   a notch filter, located at the end of the scattered light collection probe distal to the monochromator.

7. A process for characterizing the chemical composition of a sample, comprising the steps of:
   (a) placing the sample within a vacuum chamber;
   (b) performing an ESCA analysis on a selected area of the sample within the vacuum chamber; and
   (c) performing a Raman spectroscopic analysis on the same selected area of the sample within the vacuum chamber.

8. The process according to claim 7, further comprising the steps of:
   (d) bombarding the selected area of the sample with high energy ions to create freshly exposed material on the sample surface after performing steps (b) and (c) for the first time; and
   (e) Repeating steps (b) and (c).

* * * * *